(12) United States Patent
Lowman et al.

(10) Patent No.: US 7,708,979 B2
(45) Date of Patent: May 4, 2010

(54) THERMOGELLING POLYMER BLENDS FOR BIOMATERIAL APPLICATIONS

(75) Inventors: Anthony M. Lowman, Wallingford, PA (US); Michele S. Marcolongo, Aston, PA (US); Alastair J. T. Clemow, Princeton, NJ (US)

(73) Assignees: Synthes USA, LLC, West Chester, PA (US); Drexel University, Philadelphia, PA (US)

( * ) Notice: Subject to any disclaimer, the term of this patent is extended or adjusted under 35 U.S.C. 154(b) by 813 days.

(21) Appl. No.: 10/837,082

(22) Filed: Apr. 30, 2004

(65) Prior Publication Data
US 2004/0220296 A1 Nov. 4, 2004

Related U.S. Application Data (60) Provisional application No. 60/466,819, filed on Apr. 30, 2003.

(51) Int. Cl.
*A61K 49/04* (2006.01)
*A61F 13/00* (2006.01)
*A61F 2/00* (2006.01)
*A61K 31/74* (2006.01)
*A61M 31/00* (2006.01)

(52) U.S. Cl. .......... 424/9.4; 424/422; 424/423; 424/424; 424/425; 424/426; 424/78.08; 424/78.17; 604/502

(58) Field of Classification Search .......... 424/422, 424/423–426, 78.08, 78.17, 9.4; 524/916; 604/502
See application file for complete search history.

(56) References Cited

U.S. PATENT DOCUMENTS 4,954,587 A 9/1990 Mueller
5,047,055 A 9/1991 Bao et al.
(Continued)

FOREIGN PATENT DOCUMENTS

WO WO 00/62832 10/2000
(Continued)

OTHER PUBLICATIONS

Nam, I. et al., Macromolecular Research, 2002, 10(2), p. 115-121.*
(Continued)

*Primary Examiner*—Humera N Sheikh
(74) *Attorney, Agent, or Firm*—Stroock & Stroock & Lavan LLP (57) ABSTRACT

Thermogelling polymers are described containing poly (n-isopropyl acrylamide). Solutions of this polymer, copolymers or mixtures of the polymer with a second polymer such as poly(ethylene glycol), poly (vinyl pyrrolidone) or poly (vinyl alcohol) are liquids at room temperature and solids at body temperature. Thus, also provided are methods of implanting a hydrogel into a mammal by injecting the solution as a liquid at a temperature below body temperature into a selected site in the mammal at a temperature below body temperature, which then undergoes thermal phase transition to form a solid hydrogel in situ in the body as the implant warms to body temperature. Methods for using these thermal gelling materials in various applications including nucleus pulposus replacement/augmentation, wound care, disk replacement, cartilage replacement, joint replacement, surgical barriers, gastrointestinal devices, cosmetic and reconstructive surgery, and breast enlargement are also provided.

17 Claims, 5 Drawing Sheets

U.S. PATENT DOCUMENTS

| | | | |
|---|---|---|---|
| 5,192,326 A | 3/1993 | Bao et al. | |
| 5,292,415 A | 3/1994 | Mori et al. | |
| 5,976,186 A | 11/1999 | Bao et al. | |
| 6,180,326 B1 | 1/2001 | Poncelet | |
| 6,348,213 B1 | 2/2002 | Barenholz et al. | |
| 6,455,065 B1 | 9/2002 | Hymes | |
| 6,660,247 B1 * | 12/2003 | Gutowska et al. | 424/9.1 |
| 2001/0027299 A1 | 10/2001 | Yang et al. | |
| 2002/0006521 A1 | 1/2002 | Shimoyama et al. | |
| 2002/0031841 A1 | 3/2002 | Asher et al. | |
| 2003/0004533 A1 * | 1/2003 | Dieck et al. | 606/191 |
| 2004/0054413 A1 * | 3/2004 | Higham et al. | 623/17.16 |
| 2004/0091540 A1 * | 5/2004 | Desrosiers et al. | 424/486 |

FOREIGN PATENT DOCUMENTS

| | | | |
|---|---|---|---|
| WO | WO 01/05578 A1 | | 1/2001 |
| WO | WO 01/32100 A2 | | 5/2001 |
| WO | WO 01/68768 | * | 9/2001 |
| WO | WO 01/68768 A1 | | 9/2001 |

OTHER PUBLICATIONS

Kim, S. et al., Reactive and Functional Polymers, 2003, 55, p. 61-67.*
Senel et al., J. Appl. Polymer Sci., 1996, 64, p. 1775-1784.*
Zhang et al. Journal of biomaterials science 2002, 13(5):511-25.
Abhijeet Joshi et al. "The Effect of a hydrogel nucleus replacement on the compressive stiffness of the lumbar functional spinal unit" Society for Biomaterials, Annual Meeting 2003, Reno.
Supplementary European Search Report, completed Jan. 14, 2008 for European Application No. 04750971, filed Apr. 30, 2004.
Communication pursuant to Article 94(3) EPC, issued by the European Patent Office on Jun. 12, 2008, for European Application No. 04750971, filed Apr. 30, 2004.
Yuzo Kaneko et al. "Synthesis and swelling—deswelling kinetics of poly (N-isopropylacrylamide) hydrogels grafted with LCST modulated polymers" J. Biomater.Sci.Polymer Edu., 1999, vol. 10, No. 11, pp. 1079-1091, especially, p. 1079, abstract; and p. 1081, 'Methods'.
Ranee A. Stile et al. "Synthesis and Characterization of Injectable Poly(N-isopropylacrylamide)-Based Hydrogels That Support Tissue Formation in Vitro" Macromolecules, vol. 32, 1999, pp. 7370-7379.
Anthony M. Lowman and Nikolaos A. Peppas, N.A., Hydrogels, in Encyclopedia of Controlled Drug Delivery, E. Mathiowitz, Ed., John Wiley and Sons, 1999; pp. 397-418.

* cited by examiner

THERMOGELLING POLYMER BLENDS FOR BIOMATERIAL APPLICATIONS

CROSS-REFERENCE TO RELATED APPLICATIONS

This patent application claims the benefit of provisional patent application U.S. Ser. No. 60/466,819 filed Apr. 30, 2003, which is herein incorporated by reference in its entirety.

FIELD OF THE INVENTION

The present invention relates to thermogelling hydrogels which preferably are liquids at room temperature and solid, hydrogels at normal mammalian physiological body temperature. Preferred hydrogels include polymer blends or copolymers of poly(N-isopropyl acrylamide) ("PNIAAm") and a second polymer, preferably hydrophilic, such as for example poly(vinyl alcohol) or polyethylene glycol. The hydrogels have a variety of applications including, but not limited to, intervertebral disc replacement or disc augmentation, wound care, cartilage replacement, joint replacement, surgical bathers, gastrointestinal devices, drug delivery, cosmetic and reconstructive surgery, and breast enlargement.

BACKGROUND OF THE INVENTION

Hydrogels are three-dimensional, water-swollen structures composed of mainly hydrophilic homopolymers or copolymers. See, e.g., Lowman, A. M. and Peppas, N. A., Hydrogels, in Encyclopedia of Controlled Drug Delivery, E. Mathiowitz, Ed., John Wiley and Sons, 1999 pp. 397-418. These materials are for the most part insoluble due to the presence of chemical or physical crosslinks. The physical crosslinks can be entanglements, crystallites, or weak associations such as van der Weals forces and hydrogen bonds. The crosslinks provide the network structure and physical integrity. Hydrogels have been disclosed for use in a variety of biomedical applications.

Hydrogels have been used to form articles such as optical lenses. U.S. Pat. No. 4,954,587 discloses copolymers comprising a polymerization product of N,N-dimethylacrylamide, a vinyl monomer, and a cross linking agent which is machinable in a dry state and forms clear hydrogels containing 25 to 75 wt. % water. U.S. Pat. No. 5,292,415 discloses a mammalian body implant, particularly for use as a corneal prosthesis, comprising a hydrogel having azlactone-reactive nucleophilic surfaces, a multifunctional azlactone composition covalently coupled to the nucleophilic surfaces, and a biologically active material coupled to the azlactone group.

In addition to optical uses, published U.S. Patent Application 2002/0006521 discloses use of hydrogels in medical devices such as catheters and artificial kidneys and PCT Application WO 2001/05578 discloses use of hydrogels in thin film wound dressings, subcutaneous drug delivery devices and coatings for catheters. Similarly, published U.S. Patent Application 2001/0027299 discloses medical devices including dilation balloons and guide wires, catheters, stents, stent grafts, grafts, vena cava filters and inflation lumens comprising a hydrogel. Hydrophillic hydrogels have also been proposed for incorporation into flexible dermal patches for treatment of human/animal traumatic burns or skin blisters. See e.g., U.S. Pat. No. 6,348,213. Hydrogel dermal patches have also been proposed for treatment of acne and pimples. See e.g. U.S. Pat. No. 6,455,065.

Hydrogels have also been disclosed as useful materials for nucleus replacement in humans as they can be prepared with mechanical and physiological properties similar to the nucleus itself. U.S. Pat. No. 5,047,055 and U.S. Pat. No. 5,192,326 describe a hydrogel for use in nucleus pulposus replacement that is comprised of 100% semi-crystalline polyvinyl alcohol (PVA). U.S. Pat. No. 5,976,186 discloses a prosthetic nucleus prepared from hydrogels of lightly crosslinked biocompatible homopolymers and copolymers of hydrophilic monomers, HYPAN™ or highly hydrolyzed crystalline PVA, which exhibit an equilibrium, water content (EWC) of from about 30 to about 90%. WO 01/32100 discloses a modified PVA hydrogel for use in intervertebral disc replacement, and more specifically replacement of the nucleus pulposus, which has been stabilized by addition of a second polymer, preferably polyvinyl pyrrollidone (PVP) or copolymers of PVP and poly(methyl methacrylate), poly (acrylamide), poly(acrylic acid), poly(acrylonitrile) or polyethylene glycol).

Interpenetrating polymeric network hydrogels comprising temperature-sensitive poly(N-isopropyl acrylamide (PNIPAAm) have been described for use as colorimetric reagents (published U.S. Patent Application 2002/0031841) and in decontaminating, heat reversible polymer particles (U.S. Pat. No. 6,180,326). Increases in temperature have been reported to cause significant pore size decreases in interpenetrating polymeric networks composed of PNIPAAm. See Zhang et al. Journal of biomaterials science 2002 13(5):511-25.

SUMMARY OF THE INVENTION

Currently, few minimally invasive techniques exist for implantation of hydrogels into a selected site of a mammal. Typically, a surgically invasive procedure is required for insertion or implantation of a hydrogel at a selected site in a mammal. In one embodiment of the present invention, however, compositions and methods are provided which permit insertion of a hydrogel at a selected site in a mammal via percutaneous injection through a needle, insertion or injection through a cannula, or alternatively insertion or injection in a minimally-invasive surgical procedure. More particularly, in one embodiment of the invention, solutions comprising temperature-sensitive blends or copolymers of poly(N-isopropyl acrylamide) ("PNIPAAm") and a second polymer, such as for example polyvinyl alcohol) (PVA) or polyethylene glycol (PEG), are useful in production of an in situ gelling hydrogel that is a viscous liquid at room temperature (about 22 degrees C. to about 27 degrees C.) or lower and undergoes thermal transition just below body temperature (generally, from about 29 degrees C. to about 37 degrees C.) to form a solid hydrogel. In one embodiment such materials may be injected as liquids into a selected site in a mammal and then undergo thermal phase transition to a solid in situ in the body as the material warms to body temperature to form biomedical implants useful in a variety of applications.

In another embodiment, the present invention is directed towards a thermogelling hydrogel, the thermogelling hydrogel being a liquid during injection, preferable at or below room temperature, and a solid at physiological body temperature. In another embodiment, the present invention is directed towards an injectable hydrogel capable of being injected as a liquid at room temperature or below, and solidifying to form a solid implant upon warming to physiological body temperature. The injectable hydrogel preferably is capable of being injected preferably at or below room temperature in a selected site in a mammal through an about 6 gauge to about 28 gauge needle, more preferably through an about 14 gauge to about 22 gauge needle. In still a further embodiment, it is preferred that the hydrogel solution has a viscosity at temperatures ranging from about 10 degrees C. to about 27 degrees C. that could range from about 1 cP to about 25,000 cP. In one aspect the invention comprises a first polymer that is hydrophilic at about or below room temperature and hydrophobic at about 27 degrees C. and higher, and a hydrophilic second polymer. In another embodiment, the thermogelling hydrogel comprises poly(N-isopropyl acrylamide) (PNIPAAm) copolymerized and/or blended with a second polymer. In a preferred embodiment, the second polymer is hydrophilic. In yet another embodiment, the hydrogel comprises poly(N-isopropyl acrylamide) (PNIPAAm) copolymerized and/or blended with a second polymer, such as, for example, poly(ethylene glycol) (PEG), poly (vinyl pyrrolidone) (PVP) or poly(vinyl alcohol) (PVA).

In yet another embodiment, the present invention is directed towards a method of implanting a hydrogel into a selected site of a mammal which comprises injecting into a selected site in a mammal a thermogelling hydrogel wherein the thermogelling hydrogel is injected as a liquid at room temperature and solidifies to form a solid implant as the implant material warms to physiological body temperature at the selected site in the mammal. In a particular embodiment, the thermogelling hydrogel can be injected into a disc in the spinal column as a liquid to form a solid implant that replaces or augments the nucleus pulpous and is retained by the annulus of the disc. The hydrogel may be injected percutaneously through the skin of a patient directly into the disc cavity. Preferably, the hydrogel may be delivered by a syringe containing the hydrogel solution that has a needle that is inserted posteriorly into the spinal region of a patient and through the annulus of the disc. Preferably the hydrogel solution may flow through an about 6 gauge to an about 28 gauge needle more preferably an about 14 gauge to an about 22 gauge needle. In one embodiment the liquid hydrogel solution preferably has a viscosity of about 1 cP to about 25,000 cP at room temperature (about 22 degrees C. to about 27 degrees C.) or lower temperatures. Alternatively the hydrogel may be injected by a device containing a needle such as for example a syringe, at least a portion of the needle being inserted down a cannula, or alternatively the hydrogel implant can be solidified and inserted down a cannula into the disc space. Preferably, the cannula is inserted posteriorly and provides a passageway from the external posterior side of the spine to the disc annulus. The needle may pierce the disc annulus or an incision may be made in the annulus to insert the nucleus replacement implant. Alternatively the hydrogel implant may be injected or inserted by a minimally-invasive surgical procedure. The above methods may be implemented to implant in a mammal at a selected site a thermogelling hydrogel preferably comprising poly (N-isopropyl acrylamide) (PNIPAAm) copolymerized and/or blended with a second polymer. Other hydrogels described herein may be implemented by the methods described above and elsewhere in this specification.

BRIEF DESCRIPTION OF THE DRAWINGS

The foregoing and other objects, advantages and features of the invention, and the manner in which the same are accomplished, will become more readily apparent upon consideration of the following detailed description of the invention taken in conjunction with the accompanying Figure, which illustrates a preferred and exemplary embodiment, wherein.

DETAILED DESCRIPTION OF THE INVENTION

While the present invention will be described by reference to preferred embodiments, characteristics, properties and examples, it should be realized that the present invention is not limited to such specific embodiments, characteristics, properties or examples but will be defined by the claims. The present invention in one embodiment relates to novel compositions and methods that permit the insertion of a hydrogel at a selected site in a mammal via injection through the dermis by needle, by minimally-invasive procedure or by a surgical procedure. More particularly, it has now been found that polymer blends or copolymers of poly(N-isopropyl acrylamide) (PNIPAAm) and a second polymer are useful in production of an in situ gelling hydrogel that is a viscous liquid at room temperature (about 20 degrees C. to about 27 degrees C.) or lower, and undergoes thermal transition at a temperature lower than physiological body temperature (about 36 degrees C. to about 38 degrees C.) to form a solid hydrogel.

Without being bound by a particular theory, it is believed that the PNIPAAm of the blend undergoes a thermal transition between about 27 degrees C. and about 37 degrees C. and forms a hydrogel due to the insoluble nature of the PNIPAAm, which becomes entangled at the higher temperature to form physical crosslinks. It is believed that the interaction between the hydroxyl groups on the second polymer and the acrylamide groups on the PNIPAAm produce interchain hydrogen bonding, which adds mechanical structure and additional stability to the material. Further stabilization of the hydrogels can be achieved by introduction of additional physical crosslinks such as poly(vinyl alcohol) crystallites.

At about room temperature or lower, the polymer blends or copolymers are hydrophilic and solubilizes in water. When the temperature is increased above approximately 27 degrees C., however, the PNIPAAm chains become hydrophobic and collapse into a gel. The chains of the second polymer preferably remain hydrophilic, allowing the blend to absorb large amounts of water. Thus, the combination of the hydrophilic second polymer and hydrophobic PNIPAAm results in elastic hydrogels with high water content.

No cross-linking agents are required for gelation in certain embodiments of the present invention. Thus, unlike most proposed in situ gelling materials, the hydrogels of certain preferred embodiments of the present invention can be prepared by a "clean" preparation technique wherein the hydrogel is formed without concerns of leaching of unreacted, toxic monomers or cross-linking agents. Preferably, the polymers of the present invention can be injected as a viscous liquid at mom temperature, such for example at about 20 degrees C. to about 27 degrees C., or at lower temperatures, into a selected site of a mammal. The polymer blend or copolymer solidifies to form a hydrogel implant in situ at the selected site in the mammal as the implant warms to normal mammalian physiological body temperature, such as, for example, about 36 degrees C. to about 38 degrees C. The polymer blend or copolymer transitions from a liquid or slurrable solution to a solid preferably at some temperature close to but below normal mammalian physiological body temperature. The transition temperature preferably is about 27 degrees C. to about 37 degrees C. Cross-linking agents or other agents may be desirable and added to the solutions in some embodiments to tailor the temperature at which the hydrogel transitions from liquid to solid.

In a preferred embodiment, the thermogelling systems comprise a polymer blend or copolymers made from the combination of monomers of poly(N-isopropyl acrylamide) (PNIPAAm) and a second polymer in aqueous solutions. Such thermogelling systems may optionally include an imaging agent. In a preferred embodiment, the thermogelling system of the present invention comprises from about 4% to about 70% by weight of polymers in solution, more preferably from about 4% to about 62% by weight; most preferably from about 25% to about 50% by weight. In a preferred thermogelling system, the polymer blend comprises PNIPAAm and a hydrophilic polymer. More preferably, the polymer blend comprises from about 25% to about 35% of PNIPAAm and from about 5% to about 15% of a hydrophilic polymer. Most preferably, the polymer blend comprises from about 22% to about 31% PNIPAAm and from about 4% to about 13% of a second hydrophilic polymer. Examples of hydrophilic polymers suitable for use in the present invention include, but are not limited to, biocompatible polymers, such as, for example, polyethylene glycol) (PEG), poly (vinyl pyrrolidone) (PVP) or poly(vinyl alcohol) (PVA).

The polymer blends or copolymers exist in an aqueous solution within the thermogelling systems of the present invention. In a preferred embodiment, the thermogelling system comprises from about 30 weight % to about 96 weight % of an aqueous solution; more preferably from about 30 weight % to about 70 weight %; and most preferably from about 40 weight % to about 60 weight %. The water content of PVA/PNIPPAm blends preferably ranges from approximately 62% to approximately 93% by weight, approximately 38% to approximately 45% by weight for PEG MW:4600/PNIPAAm blends and approximately 55% to about 82% for PEG MW:8000/PNIPAAm blends. Typical examples of aqueous solutions suitable for use in the thermogelling systems of the present invention include water, saline solution, and buffered phosphate solutions.

In a first exemplary embodiment of the present invention, the thermogelling system comprises a solution of linear homopolymers of PNIPAAm and a second hydrophilic polymer that form a gel consisting of a blend of the two. In a second exemplary embodiment of the present invention, the thermogelling system comprises PNIPAAm grafted to a second polymer comprising a hydrophilic chain. In a third exemplary embodiment of the present invention, the thermogelling system comprises a second polymer comprising hydrophilic side chains grafted or co-polymerized to a PNIPAAm backbone to form a branched or grafted structure. In a fourth exemplary embodiment, the thermogelling system of the present invention comprises diblock polymers of PNIPAAm and a second polymer comprising a hydrophilic component. In yet a fifth exemplary embodiment, the thermogelling system comprises A-B-A triblock copolymers where PNIPAAm is the center B block and the second polymer comprising a hydrophilic polymer is the outer A block. Furthermore, any of the above exemplary embodiments of homopolymers or copolymers may be blended with any of the other homopolymers or copolymers.

The mass ratio of the polymer blends or copolymers in the thermogels of the present invention preferably ranges from about 500:1 (wt:wt) PNIPAAm:second polymer to 1:500 PNIPAAm:second polymer with a preferred range of 20:1 (wt:wt) to 1:20 (wt:wt). Increasing the amounts of PNIPPAm generally increases the ability of the solution to gel and solidify at elevated temperatures. Preferred ratios of PNIPAAm:second polymer are 3:1, 2:1, 1:1, 1:2, and 1:3 for a second polymer solution such as PVA or PEG of 5 to 10%, and a PNIPAAm solution of 25 to 35%. More preferred ratios of PNIPAAm:second polymer ratios include ratios of about 1:1 to about 3:1 (wt:wt). The weight average molecular weight of the polymer chains or blocks is expected to range from about 1000 Da to about 10,000,000 Da, preferably from about 1000 Da to about 100,000 Da.

In an alternative embodiment, the polymers that comprise thermogelling hydrogel of the present invention can be injected into a selected site of a mammal in a dry or dehydrated state, rather than in the form of a solution as described above. In one embodiment, the dry solid polymers that comprise the hydrogel can be injected directly into a selected site of a mammal, such as, for example, the disc cavity. Alternatively, the dry hydrogel materials can be inserted inside the disc cavity by means other than injection. Alternatively, or in addition to, the dry hydrogel materials may be introduced into a containment device. The containment device, and the dry hydrogel materials contained therein, can then be implanted into a selected site of mammal. The containment device is preferably semi-permeable and retains the hydrogel material and allows for passage of water into and out of the hydrogel material. In either embodiment, the dry hydrogel materials preferably become physically entangled in vivo upon injection into the body and preferably swell or inflate by absorption of water from the surrounding body fluids. The dry hydrogel, with or without the containment device, may be transported by a holding device such as a spatula, forceps or other device. In either situation, an incision may be required in the annulus of the disc in order to implant the dry hydrogel. After insertion, the incision may need to be sutured or otherwise closed to retain the implant. It is contemplated that the implant upon insertion may swell so that suturing or closing of the incision may be unnecessary.

The dry hydrogel material preferably comprises PNIPAAM and a second hydrophilic polymer. Preferably, the second hydrophilic polymer comprises PEG, PVP or PVA. The dry or dehydrated hydrogel materials can take the form of, for example, powders, particulates, beads, granules, bulk materials, etc. In a preferred embodiment, the containment device with the hydrogel material contained therein can be folded and implanted in the nucleus through a very small window on the annulus either in open surgery or minimally invasive after the degenerated nucleus has been removed. The dry hydrogel, with or without the containment device, may be transported to the disc space through a cannula or other opening that provides access and a passageway to the disc. The tip of the cannula may contact the portions of the outer surface of the disc annulus or the tip of the cannula may be inserted into the incision in the disc annulus. Suitable materials for use as the containment device in the context of the present invention are preferably conformable and aptly resistant to tearing or rupture when in use. The containment device is preferably formed of a material that does not substantially bond to the dry hydrogel materials such that the dry hydrogel materials are free to move or flow at least to a limited extent within the device. The containment device may be in the form of, for example, a membrane, a flexible cover, an envelope, a sac, or a bag, and preferably, is permeable to water and bodily fluids. The degree of permeability may be chosen by one of ordinary skill in the art so as to control the role of diffusion of water or other body fluids, and thus, the rate of absorption by the hydrogel polymer materials and inflation of the hydrogel. Suitable materials for forming the containment device include, but are not limited to, woven, braided and non-woven materials, which may be fibrous or non-fibrous, such as, for example, plastic films. The containment device may consist of a single layer or it may be multi-layered. Further, it may be strengthened with reinforcement means, such as an additional layer of a resilient material or a reinforced fiber composite structure.

Exemplary materials suitable for forming the containment device include, but are not limited to, polyethylenes (which may be ultra high molecular weight polyethylenes), polyester, polyurethane, polyesterurethane, polyester/polyol block copolymer, polyethylene terephalate, polytetrafluoro-ethylene polyester, nylons, polysulphanes, cellulose materials, and combinations thereof. In a preferred embodiment, the containment device comprises a water permeable or semi-permeable membrane. Water permeable membrane materials said to be suitable for use in disc nucleus prostheses are disclosed in U.S. Pat. No. 5,192,326, which is hereby incorporated by reference. The thermogelling hydrogel of the present invention, when in its dehydrated or dry form, can be introduced into a selected site of a mammal by any appropriate technique. Preferably, the technique is minimally-invasive. In one embodiment, the containment device with the dry polymer hydrogel materials present therein is introduced into a disc nucleus space in the form of a flexible membrane or cover (such as, for example, a sac or bag), which may be folded, rolled up, or otherwise stowed in its unexpanded or partially expanded state, by means of an aperture or incision in the annulus fibrosis (which may be made by a surgeon or which may have already occurred to a damage or aging of the fibrous).

The containment device is desirably configured so as to adopt a shape generally conforming to that of the natural disc nucleus pulposis when expanded to a certain degree. In one embodiment, the dry hydrogel polymer materials can be introduced into the containment device via injection through a valve. This can be done using a hypodermic syringe. Alternately, the dry hydrogel polymer materials are simply placed inside the containment device when said containment device takes the form of, for example, an envelope, bag or sac.

In addition, the thermogelling systems of the present invention may optionally include an imaging agent. The inclusion of an imaging agent allows the user to image the sample as it is injected into the body, thereby assisting in the proper placement of the implanted hydrogel because the implanted material can be visualized under X-rays. Imaging agents preferably may be included in the thermogelling systems of the present invention in amounts up to about 25% by weight. In a preferred embodiment, the thermogelling system comprises from about 2 weight % to about 25 weight % of an imaging agent; more preferably from about 7 weight % to about 15 weight %. In a particularly preferred embodiment, the thermogelling system comprises about 11 weight % of an imaging agent. Typical imaging agents suitable for use in the present invention include barium sulfate, iodine, or any heavy metal powder that provides the necessary radio-opacity under external imaging. The imaging agent is added to the thermogelling system while the system exists in a liquid phase and is mixed therein to preferably obtain uniform distribution in the solution.

The hydrogels of the present invention, once solidified, may exhibit mechanical as well as biocompatible properties that render them suitable for implantation in mammals. Such implants are useful in a variety of applications including, but not limited to, wound care, disc replacement or augmentation, cartilage replacement, joint replacement, surgical barriers, gastrointestinal devices, cosmetic and reconstructive surgery, and breast enlargement. Accordingly, the present invention is further directed towards methods of implanting a hydrogel into a selected site of a mammal which may comprise injecting into a selected site in a mammal a thermogelling hydrogel comprising poly(N-isopropyl acrylamide) (PNIPAAm) copolymerized and/or blended with a second polymer. The thermogelling hydrogel is injected into the selected site in a mammal as a liquid at room temperature and solidifies to form a solid implant as the hydrogel warms to physiological body temperature at the selected site in the mammal.

In one embodiment, thermogelling hydrogels of the present invention, once solidified, exhibit adequate mechanical properties as well as biocompatibility to serve as a useful prosthetic nucleus for replacement or augmentation of nucleus pulposus in spinal discs in mammals, including humans. Particular applications of the hydrogel may be useful for replacement or augmentation of nucleus pulpous in spinal discs in mammals, including humans, diagnosed with early degenerative disc disease. In a particular embodiment, the thermogelling hydrogel can be injected into a cavity formed by the annulus of a spinal disc as a liquid to form a solid implant in situ that is retained by the annulus of the disc. One of skill in the art can inject the polymer blends of the present invention in their viscous liquid state into the nuclear cavity of an intervertebral disc using a standard microdiscetomy approach. In one embodiment, the hydrogel can be injected percutaneously through the skin directly into the cavity formed by the annulus of the disc.

Figure 1:
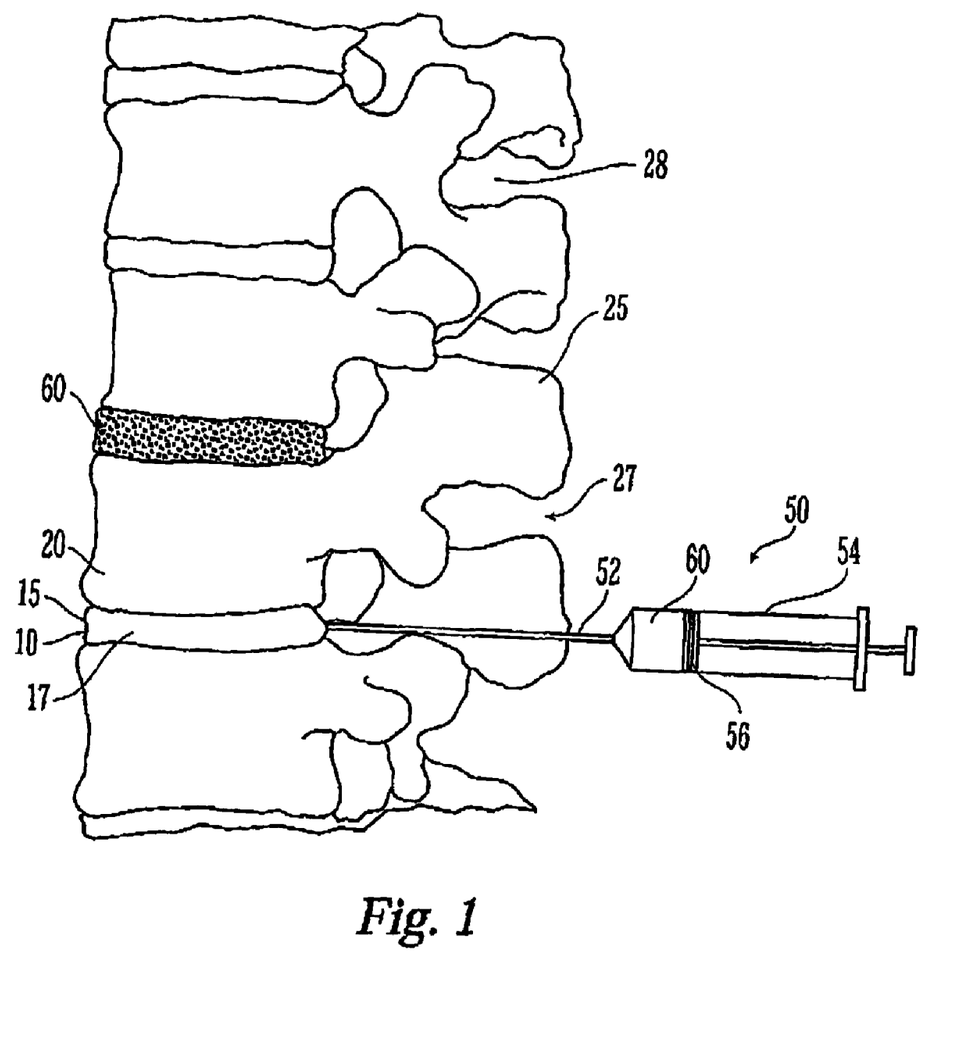
FIG. 1 illustrates the injection of the hydrogel posteriorly into the spinal region of a patient and through the annulus of the disc using a syringe that contains the hydrogel solution and that has a needle.

More preferably, as shown in FIG. 1, the liquid hydrogel 60 can be inserted from the posterior side 27 of the spinal column 28 past the spinous process 25 into the cavity 17 formed by the annulus 15 of the disc 10, using a syringe 50 that contains the hydrogel solution 60. Typically, the syringe 50 contains a needle 52, and uses to plunger 56 that can be adjusted to expel the hydrgogel solution 60 from the syringe housing 54, FIG. 1 also demonstrates the visualization of the solid hydrogel with an imaging agent 62 in the disc 10 following injection of the hydrogel solution 60 and subsequent solidification as the hydrogel solution 60 warms to physiological body temperature.

In an alternate embodiment, the hydrogel can be injected through one or more cannulas (or other device) that have been inserted into the patient down to the disc site in order to create access to the annulus. In this regard, the cannula provides a passageway from outside the patients body down to the disc, preferably in a manner where the user can visualize where the needle will be inserted into the disc or the incision in the disc annulus will be made. In yet another embodiment, the hydrogel can be injected into a selected site of a mammal by a minimally-invasive surgical procedure. The viscosity of the solutions injected at temperatures ranging from about 10 degrees C. to about 27 degrees C. preferably range from about 1 cP to 25,000 cP depending on the application. The hydrogels in one embodiment may be injected by using devices having a needle that ranges from about 6 gauge to about 28 gauge, with preferred devices containing an about a 14 to about 22 gauge needle. The present invention could be used for complete replacement of the nucleus puloposus or simply as an augmentation following injury or partial discectomy. Implantation of the prosthetic nucleus is expected to provide relief from pain as well as provide for functional disc activity.

For the nucleus pulposus replacement or augmentation to be successful, in addition to biocompatibility of the material in general and the appropriate local tissue response at the site of implantation, there are several mechanical requirements which preferably will be achieved. The nucleus replacement biomaterial should provide adequate tension to the annulus fibrosus upon loading in order to tension the annulus fibers and thereby restore biomechanical behavior of the disc to that of the normal intervertebral disc. The biomechanics of the restored disc should behave similar to the intact disc in compression, flexion and torsion. In addition, the device should restore the time dependent biomechanical behavior so that the implanted disc behaves similar to the intact normal disc in creep and stress relaxation. Fatigue of the implant in the disc should be able to withstand the life of the patient without degradation to the point of necessitating a revision surgery. Preferably there should be no appreciable wear debris from the device in the disc space necessitating a revision surgery due to pain or inflammation. It may or may not be desirable to appear radiopaque upon X-ray. Also, the nucleus replacement or augmentation would ideally be able to be implanted in a minimally invasive manner or injected percutaneously.

To accomplish the goals of the device, the biomaterial itself should display certain material properties. The material should have a modulus of elasticity and Poisson's ratio such that a complete filling of a nucleus cavity or an augmentation to a nucleus cavity to a given pressure or disc height will succeed in restoration of the biomechanical behavior of a normal disc. One way that the implant material can provide an interfacial stress on the annulus fibrosus inner surface is through the Poisson effect. The material can, upon loading, deform radially. With an elastomeric material, such as the hydrogel family, a relatively high Poisson ratio, in the range of about 0.35 to about 0.4999 can be achieved. The higher the Poisson ratio, the higher the interfacial stress can be transmitted to the tumulus and potentially more complete restoration of biomechanics can be achieved.

Additional mechanical behavior of the implant material is important. The material should be able to withstand from about 10 million to about 40 million cycles of compression-compression fatigue to physiological loading levels for the nucleus. Shear fatigue will also be an important material property because of the off-axis loading that may take place during the life of the device. Time-dependent behavior of the implant material should be such that the material can creep over a constant activity load (for example, standing or walking during the day) but be able to fully or nearly fully recover from the deformation during the resting state of the device (for example, while the patient is lying prone in a resting state where the load levels are much lower than the active state). The natural disc undergoes creep and recovery in a diurnal cycle and if the implant material also undergoes a similar mechanical behavior, it is important that it be in a similar time frame. The wear properties of the material are also important, and the wear debris produced from the device, if any, should be in a form that does not cause an unacceptable inflammatory response that would lead to permanent and irreparable damage to the surrounding tissues at or near the implantation site.

The modulus of elasticity has an effect on the ability of nucleus replacement implants to perform successfully. Compressive biomechanics similar to a fully functional disc are achieved with a modulus of elasticity from about 10 KPa to about 10,000 KPa and normal mechanical behavior is restored with a modulus of elasticity from about 10 KPa to about 5,000 KPa. More preferably an implant modulus of about 50 KPa to about 1,500 KPa is in a range to restore the compressive stiffness. It is contemplated that a threshold exists where the modulus of the implant affects tensioning the annulus fibers, after which the lateral deformities associated with the higher modulus do nothing to further the stiffness of the system.

Testing has shown that insufficient filling of the nucleus cavity contribute significantly to the stiffness of the disc and its performance in the spinal column. More specifically, the effect of height and diameter variation has a significant effect on the stiffness of the disc. In cases where a denucleated disc is not restored to its intact normal diameter and height, the lack of proper interaction between the hydro gel implant and the annulus resulted in limited restoration of the functional spinal column unit. The functional spinal column unit referring to a disc and two adjoining vertebrae. However, in cases where the denucleated disc is fully expanded or restored to its normal intact height and/or diameter almost complete restoration of the stiffness is observed. Testing has further shown that expanding a denucleated disc to more than its normal intact height, or expanding the denucleated disc to more than its normal intact diameter (width) provides almost complete restoration of the stiffness of the disc.

With the injectable hydrogels according to one aspect of the invention, restoring the "fit and fill" of the disc easily be achieved by the amount of hydrogel solution that is injected. By varying the amount of hydrogel solution injected into the disc cavity, the fit and fill of the disc can be tailored for each disc and each patient during the procedure, which is advantageous over preformed implants. In addition, discs can be "overfilled" with the injectable hydrogels of the present invention without compromising the performance of the disc. The amount of hydrogel solution that may be injected into a typical patient disc should preferably be proportional to the volume of the cavity that the implant is intended to fill. Such a cavity may be created, for example, from a nucleotomy. In one embodiment, the ratio of the volume of the hydrogel solution to be injected into the cavity ("implant volume") to the volume of the cavity ("cavity volume") is preferably about 0.8 to about 1.5. In a preferred embodiment, the implant volume-to-cavity volume ratio should be about 1.0 to about 1.13. These volume ratios are illustrative only and may vary by the size of the patient and the specific disc that needs to be restored. For the purposes of determining such ratios, the volume of the cavity can be approximated, for example, from the radius of the cavity (r) and the disc height (h) using the following equation $V=\pi r^2 h$. See Joshi et al., Society for Biomaterials, Annual Meeting 2003, Reno.

The hydrogels of the present invention can be used in a number of other medical applications as well including, but not limited to, cartilage replacement, plastic and reconstructive surgery and bariatric or obesity surgery where the ability to introduce a material through a small needle or incision and then allow it to solidify at body temperature is advantageous. For example, in the first of these applications, a low viscosity polymer solution may be injected into an arthritic joint cavity to fill defects in the hyaline cartilage. As the material warms to its transition temperature and solidifies, the hydrogel can act as a defect filler to inhibit or delay further cartilage damage. In plastic and reconstructive surgery, indications for use of the hydrogels include, but are not limited to, repair and reconstruction of body parts (nose, ear, chin etc.) as well as augmentation of other parts such as breast or, muscles and as an aid to wrinkle removal. For bariatric surgery, a minimally invasive or percutaneous injection of the hydrogel into the fining of the stomach or into a balloon placed within the stomach can act to limit the overall size of the stomach, leading to a feeling of satiation and a reduction in the desire to further eat. Hydrogels of the present invention are also useful in urological surgery to augment bladder control and in gastrointestinal surgery where, for example, the hydrogel can be injected into the esophageal sphincter to reduce the damage to the esophagus caused by gastrointestinal reflux disease.

Further, it is expected that those of skill in the art will develop additional surgical uses for the hydro gels of the present invention based upon the teachings herein. The following non-limiting examples are provided to describe methods of making embodiments of the hydrogel and to further illustrate embodiments of the present invention.

EXAMPLES

Example 1

Preparation of PVA/PNIPAAm

PNIPAAm was synthesized through a free radical solution polymerization. The reaction was carried out at 60 degrees C. for 2 hours. After polymerization, methanol was evaporated and the resulting polymer was dried overnight in a vacuum oven. Excess monomer was removed by dissolving the dried polymer in water at room temperature and then raising the temperature to 50 degrees C. The water phase, containing the excess monomer, was then poured off. This process was repeated until all unreacted residual monomer was removed.

Example 2

Screening of Gelation of PVA/PNIAAm Blends

Screening studies were performed to help define regions of polymer concentrations that provide for thermogelling behavior. Initially, aqueous PVA solutions of 5, 10, and 15% w/v, and PNIPAAm solutions of 15, 25, 35, and 45% w/v were created. The PVA solutions were combined with PNIPAAm solutions in volumetric ratios of 1:1, 1:5, and 1:10. The two solutions were mixed to form a miscible solution at room temperature. The gelation behavior at physiological temperature is shown in Table 1. The appearance of the hydrogel was then classified as solid (S), semi-solid (SS), or liquid (L). The solid (S) designation was used for materials that remain solid and did not extrude liquid upon application of pressure (approximately 1-2 lbs. of force) from a hand-held laboratory spatula. Semi-solid (SS) designation was used for systems that exhibited two-phase behavior at 37 C with one part solid and one part liquid. The liquid (L) designation was used for samples that remained liquid; that is, samples remaining as a solution or slurry.

TABLE 1

Gelation screening of PVA/PNIPAAm blends.

| | | PNIPAAM CONCENTRATIONS | | | |
|---|---|---|---|---|---|
| | | 15% | 25% | 35% | 45% |
| PVA Concentrations | 5% | 1:1(SS) | 1:1(S) | 1:1(S) | 1:1(S) |
| | | 1:5(L) | 1:5(L) | 1:5(SS) | 1:5(SS) |
| | | 1:10(L) | 1:10(L) | 1:10(L) | 1:10(-)* |
| | 10% | 1:1(L) | 1:1(S) | 1:1(S) | 1:1(S) |
| | | 1:5(L) | 1:5(L) | 1:5(L) | 1:5(SS) |
| | | 1:10(L) | 1:10(L) | 1:10(L) | 1:10(L) |
| | 15% | 1:1(L) | 1:1(S) | 1:1(SS) | 1:1(S) |
| | | 1:5(L) | 1:5(SS) | 1:5(S) | 1:5(S) |
| | | 1:10(L) | 1:10(L) | 1:10(L) | 1:10(L) |

*(-) indicates that the two polymer solutions were immiscible.

Example 2

Screening of Gelation Properties of PEG/PNIPAAm Blends

Similar gelation screening was performed with PEG solutions of 5, 10, 25 and 50% w/v, and PNIPAAm solutions of 25 and 35% w/v with PEG molecular weight 4600 and with PEG solutions of 5, 10 and 25% w/v, and PNIPAAm solutions of 25 and 35% w/v with PEG molecular weight 8000. The PEG solutions were combined with PNIPAAm solutions in volumetric ratios of 1:1 and 2:1. The gelation behavior at physiological temperature is shown in Tables 2 and 3.

TABLE 2

Gelation screening of PEG MW:4600/PNIPAAm blends

| | | PEG:PNIPAAm | |
|---|---|---|---|
| PEG WM:4600 | | 1:1 | 2:1 |
| PNIPAAm/ | 25/5 | SS | S |
| PEG | 25/10 | S | S |
| Concentrations | 25/25 | S | SS |
| | 25/50 | L | L |
| | 35/5 | S | S |
| | 35/10 | S | S |
| | 35/25 | S | SS |
| | 35/50 | L | L |

TABLE 3

Gelation screening of PEG MW:8000/PNIPAAm blends

| | | PEG:PNIPAAm | |
|---|---|---|---|
| PEG WM:8000 | | 1:1 | 2:1 |
| PNIPAAm/ | 25/5 | S | S |
| PEG | 25/10 | S | S |
| Concentrations | 25/25 | SS | L |
| | 35/5 | S | S |
| | 35/10 | S | S |
| | 35/25 | SS | L |

Example 3

Gelation Screening of PNIPAAm-Grafted PEG Polymers

PNIPAAM grafted PEG was prepared by solution polymerization of NIPAAM and PEG monomethacrylate (PEGMA). Polymers with varying ratios of the monomers were prepared. Solutions of 25, 30 and 50% w/v in water were prepared at room temperature. The gelation behavior at physiological temperature is shown in Table 4.

TABLE 4

Gelation Screening of PNIPAAM-Grafted PEG Polymers

| Ratio of | Solution Composition w/v % | | |
|---|---|---|---|
| NIPAAM/PEGMA | 25% | 30% | 50% |
| 10:1 | L | L | SS |
| 20:1 | SS | SS | SS |
| 50:1 | S | S | SS |
| 100:1 | S | S | S |
| 500:1 | S | S | S |

Example 4

Gelation Screening of PNIPAAm-Branched PEG Polymers

PNIPAAM branched PEG was prepared by solution polymerization of NIPAAM and PEG dimethacrylate (PEGDMA). Polymers with varying ratios of the monomers were prepared. Solutions of 25, 30 and 50% w/v in water were prepared at room temperature. The gelation behavior at physiological temperature is shown in Table 5.

TABLE 5

Gelation Screening of PNIPAAM-Grafted PEG Polymers

| Ratio of NIPAAM/PEGDMA | Solution Composition w/v % | | |
|---|---|---|---|
| | 25% | 30% | 50% |
| 5:1 | L | L | L |
| 10:1 | L | L | L |
| 20:1 | L | L | L |
| 50:1 | SS | SS | S |
| 100:1 | SS | S | S |
| 200:1 | S | S | S |
| 500:1 | S | S | S |

Example 5

Gelation Screening of PEG-PNIPAAm-PEG Triblock Polymers

PEG-PNIPAAM-PEG triblocks were prepared using monomethoxy terminated PEG and difunctional (COOH-terminated) PNIPAAm. The PNIPAAm was synthesized with 3 molecular weights (low, med., high). Solutions of the triblocks were prepared at concentrations of 30 and 50% w/v in water at room temperature. The gelation behavior at physiological temperature is shown in Table 6.

TABLE 6

Gelation Screening of PEG-PNIPAAm-PEG Triblocks Polymers

| | Solution Composition w/v % | |
|---|---|---|
| | 30% | 50% |
| PEG-low PNIPAA-PEG | L | S |
| PEG-medium PNIPAAM-PEG | SS | S |
| PEG-high PNIPAAM-PEG | SS | S |

Example 6

Hydrogel Stress-Strain Testing

In an exemplary embodiment, N-Isopropylacrylamide (NIPAAm) (FW=113.16 g/mol) was purified by dissolving in hexane and heating to 55 degrees C. for about 30 min. The solution was then placed into a refrigerator at 5 degrees C. until the monomer crystallized. The monomer was then vacuum filtered, placed into a weigh boat, and dried under vacuum overnight to remove solvent.

Purified NIPAAm was then polymerized with either poly(ethylene glycol) monomethyl ether monomethacrylate 1000 (PEGM 1000, FW=1100.06 g/mol) or poly(ethylene glycol) dimethacrylate 1000 (PEGDM 1000, FW=1154.09 g/mol) in 200:1 weight ratios (200 grams NIPAAm/1 gram functionalized PEG) in methanol solvent. The reactions were initiated with 2,2-Azobisisobutryronitrile (AIBN, FW=164.21 g/mol) with a 116:1 weight ratio of purified NIPAAm to AIBN. Reaction mixtures were bubbled with $N_2$ for approximately 3 min and then heated at 65 degrees C. for 2 hr. After 2 hr, the reactions mixtures were removed from the bath and quenched in a refrigerator. The reaction mixtures were then stirred in a hood overnight to evaporate the methanol solvent. The dried polymers were then ground to a fine powder.

After the methanol was removed from the polymers, the polymers was purified by completely dissolving them in deionized ("DI") water and heating to 37 degrees C. (above its lower critical solution temperature ("LCST")) for approximately 20 min. The precipitated polymers were then removed from solution and dried overnight in a weigh boat to remove water. The polymer was further dried for about 48 hours in a vacuum oven.

The dried polymers were then ground to a fine powder. DI water was added to the powders to create 25% aqueous solutions. The solution was vortex mixed and left to sit for about 48 hours.

The solutions were then poured into a 14.5-mm ID annular ring and the ring was heated to 37 degrees C. to precipitate the polymer in solution. The formed hydrogels were removed from the ring after 5-10 min and were swelled in DI water at 37 degrees C. for 24 hours prior to mechanical testing.

Unconfined Compression

The cylinders were compressed using an Instron mechanical testing system (Intron Model 4442, Canton, Mass.) fitted with a 50-N load cell and 37 degrees C. water bath. Samples were compressed at a strain rate of 100%/min. Load and displacement data was recorded at 20 points/sec with the Instron Series IX software. This data was converted to stress and strain values in Microsoft Excel using the sample's initial dimensions. A tangent compressive modulus for each hydrogel sample was calculated at 15, 20, and 25% strain. The average slopes of the stress/strain curve between 10 and 20%, 15 and 25%, 20 and 30% were assumed to be equal to the tangent slopes at 15, 20, and 25% stain respectively, Confined Compression A confined compression test was performed by fitting an Ingstron mechanical testing system (Model 4442, Canton, Mass.) with a 50-N load cell and 37 degrees C. water bath to a confined testing configuration, Samples were compressed at a strain rate of 100%/min. A cylindrical plunger composed of 316 stainless steel was compressed upon the gel as it was confined by a high density polyethylene ring having a 11.7-mm ID. The ring was assumed to be effectively rigid as its stiffness was magnitudes higher than that of the polymer sample it surrounded. Load and displacement data was recorded at 20 points/sec with the Ingstron Series IX software. This data was converted to stress and strain values in Microsoft Excel using the sample's initial dimensions. A confined compression modulus was measured as the slope of the stress-strain response in the final linear region after the initial toe-in region (below 0.001 MPa) was removed. The slope was measured with data points in the curve that exceeded 0.15 MPa (just prior to load limit of load cell was reached) to ensure the sample was confined.

Results

Figure 2:
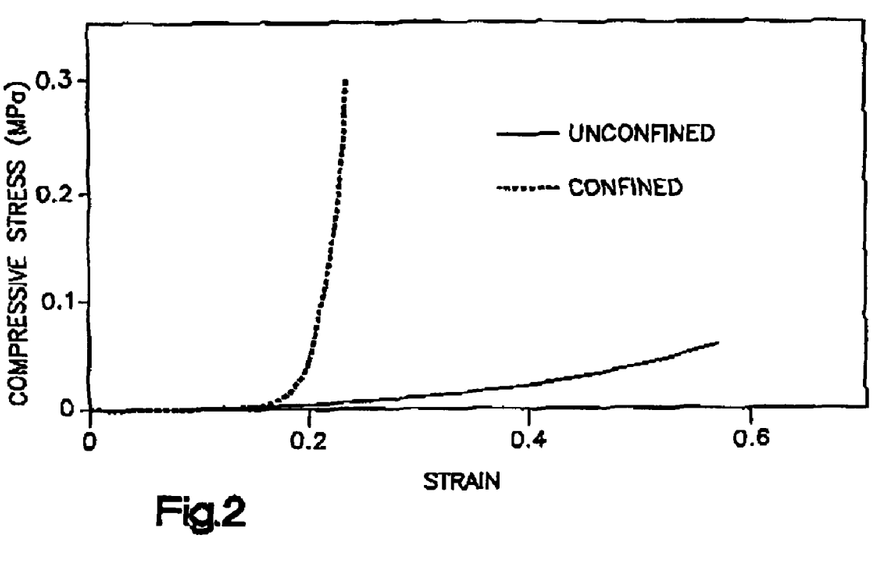
FIG. 2 illustrates the typical stress/strain response of injectable polymer under confined and unconfined compression.

Unconfined compression tests showed a hyper-elastic response for each polymer tested. A typical stress/strain response of the gels in unconfined compression is shown in FIG. 2.

Figure 3:
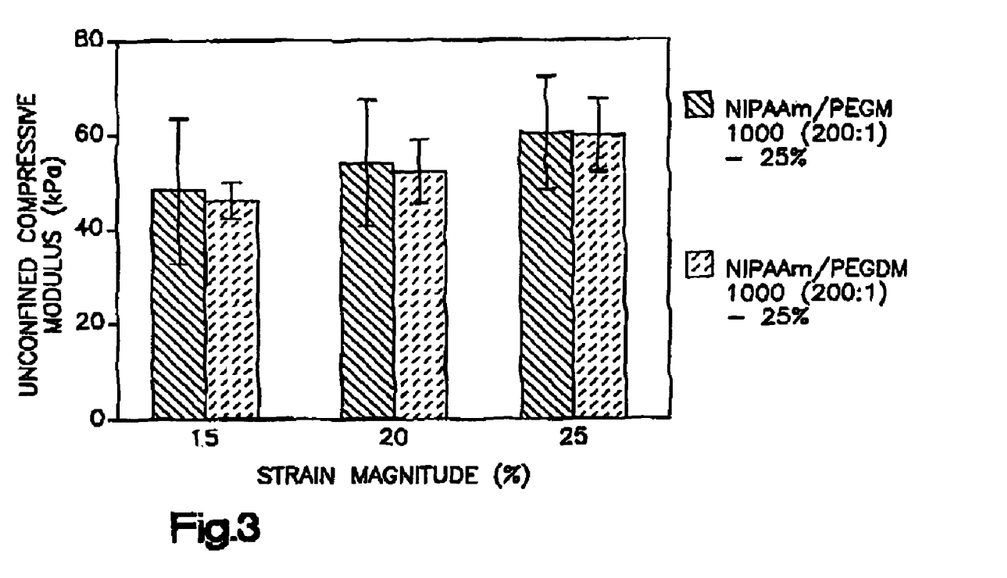
FIG. 3 illustrates the unconfined compression modulus values of polymer systems.

Unconfined compressive modulus values for the polymers tested in this study (FIG. 3) were similar at 15%, 20%, and 25% strain magnitude. Error bars represent. +−. one standard deviation.

Figure 4:
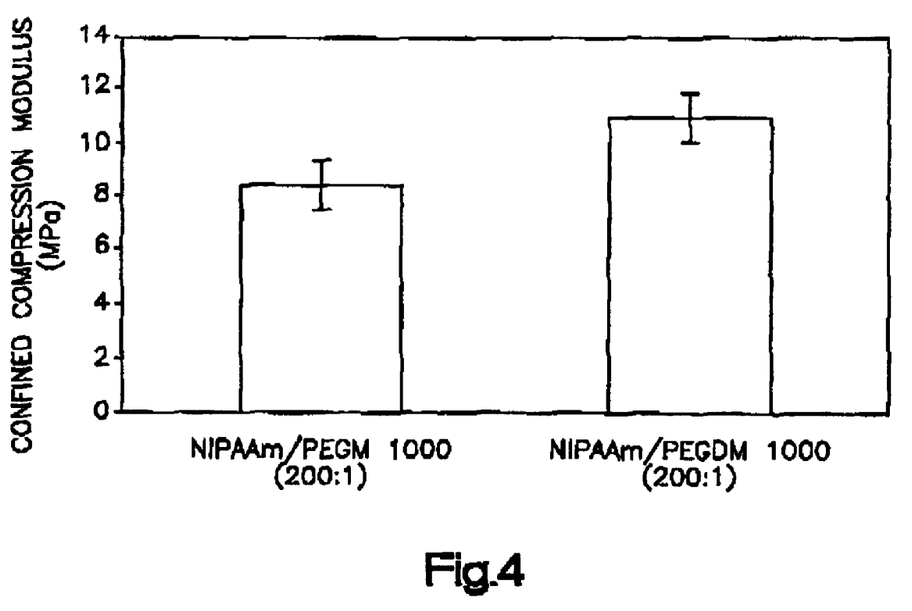
FIG. 4 illustrates the confined compression modulus values of polymer systems.

Confined compression tests resulted in a drastically different stress/strain response as shown in FIG. 1. The confinement of the polymer caused the stress measured by the axial load cell to increase drastically once the unbound water within the larger polymer pores was pressed out of the gel. The strain when this occurs depended on the compressibility of the polymer network. Extrinsic properties such as inaccurate polymer volume measurements and cylinder aspect ratio (height/diameter) also seemed to have a big influence on the strain magnitude when confinement occurred and the slope of the stress/strain curve as the load reached the limit governed by the load cell (50N). The confined compressive modulus values that were calculated from these experiments are shown in FIG. 4. The polymer composed of PNIPAAm with PEG branches (reaction with PEGDM 1000) had a 32% higher confined compression modulus than the polymer containing PNIPAAM with PEG tethers.

These tests represent the initial experiments to compare confined and unconfined compression responses of injectable polymers. This data indicates that the materials have the necessary mechanical properties to function as a synthetic nucleus.

Example 7

Hydrogel Visualization

The ability of the thermogelling polymers to be visualized under standard X-Ray examination was demonstrated by taking a hydrogel containing a solution of 22% 200:1 PNIPAAM-branched PEGDMA hydrogel, 66% water and 11% by weight barium sulfate powder. The barium sulfate was dispersed by sonic agitation at room temperature. The resultant hydrogel was injected into a disc, and then visualized using a standard C-Ann X-ray machine.

Example 8

Comparison of Modulus of Elasticity and Geometric Parameters on Compressive Stiffness The effect of variation in the hydrogel nucleus implant material (modulus) and geometric (height and diameter) parameters on the compressive stiffness of the human lumbar functional spinal unit have been examined. As used throughout this example, the term anterior column unit ("ACU") refers to a segment of the spine that consists of two vertebrae with posterior elements removed and a disc. A 10% polymer mixture was prepared from a blend of poly (vinyl alcohol) (PVA) (MW=138,400-146,500) and poly (vinyl pyrrolidone) (PVP) (MW=10,000) to make hydrogel implants. The blend was prepared with a composition of 95% PVA/5% PVP. The polymer solution was cast into the custom made molds of three different diameters ($D_1$=15 mm, $D_2$=16 mm, $D_3$=17 mm). Specimens were prepared in three heights ($H_1$=$H_{2-1}$ mm, $H_2$, $H_3$=$H_{2+1}$ mm), where $H_2$ is the average intervertebral disc ("IVD") height of the tested ACU. Three implant moduli were studied, a first modulus ($E_1$=50 KPa @ 15% strain), a second modulus ($E_2$=150 KPa @ 15% strain), and a third higher modulus implant ($E_3$=1.5 MPa @ 15% strain) was made from Silastic T2, a commercially available polymer mixture (Dow Corning®).

Lumbar spines were harvested from four cadavers (1 male, 3 females) with an average age of 63-years. ACUs (n=9) from L1-L5 levels were resected and prepared by removing the facet joints and ligaments. Parallel axial cuts normal to the longitudinal axis of the ACU were made in the vertebrae above and below the disc to ensure alignment of an axial compression load.

Mechanical testing was performed on an Instron mechanical test machine (Model 1331). A series of compressive tests were run on each of the nine specimens using a previously validated test protocol. See Joshi et al., Society for Biomaterials, Annual Meeting 2003, Reno. First intact specimen was tested. The upper vertebra was then core drilled (16 mm diameter) along the ACU longitudinal axis from the proximal cut surface through the upper end plate. This drilling created a bone plug, which remained in its original position and the specimen was tested again ("BI condition"). The bone plug was then removed, the nucleus pulpus ("NP") was excised in-line with the 16 mm core drilling of the upper vertebrae and the specimen was again tested (DN condition). A parametric study of the effect of NP implant moduli, heights and diameters was then conducted by inserting the appropriate NP implant into the disc, replacing the bone plug and repeating the test protocol.

For each specimen, implant modulus was varied ($E_1$/$E_2$/$E_3$) with a constant implant height ($H_2$) and diameter ($D_2$). Similarly, implant height was varied ($E_1$/$E_2$/$E_3$) with a constant implant modulus ($E_2$) and diameter ($D_2$). Finally, implant diameter was varied ($D_1$/$D_2$/$D_3$) with a constant implant modulus ($E_2$) and height ($H_2$). For each specimen, the order of the testing was chosen randomly to minimize any effect of implant parameters on the test specimen. At end of the experiment, the specimen was re-tested in the denucleated condition (DN−1).

Denucleation of the specimen (DN condition) significantly reduced the compressive stiffness of the specimen in comparison to the BI condition at 15% strain ($p<0.001$). Insertion of NP implants restored the compressive stiffness of the denucleated specimen to that of the BI condition ($p>0.05$) except for $H_1$ and $D_1$ conditions ($p=0.01$). The stiffness of DN and DN−1 conditions were not different ($p>0.05$). ACU compressive stiffness was not significantly different ($p>0.05$) comparing moduli $E_2$ and $E_3$. All other parametric conditions showed significant differences ($p<0.05$) in ACU compressive stiffness.

Figure 5A:
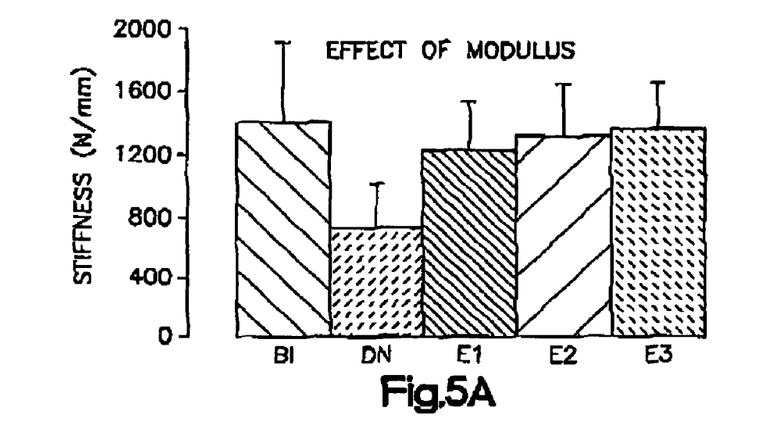
FIG. 5 illustrates the compressive stiffness of different testing conditions.
Figure 5B:
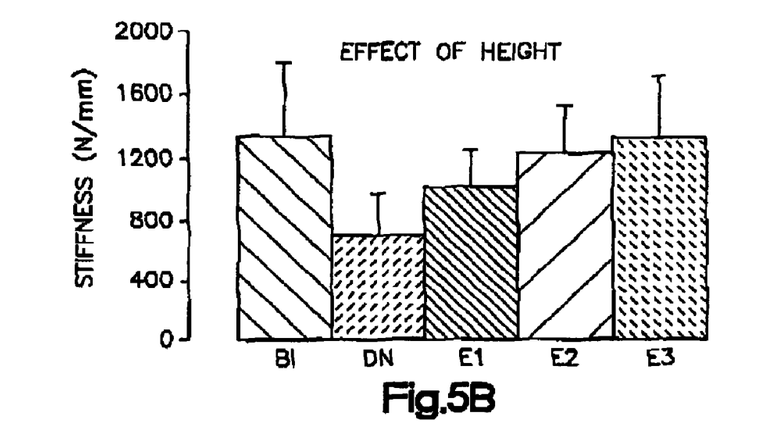
Figure 5C:
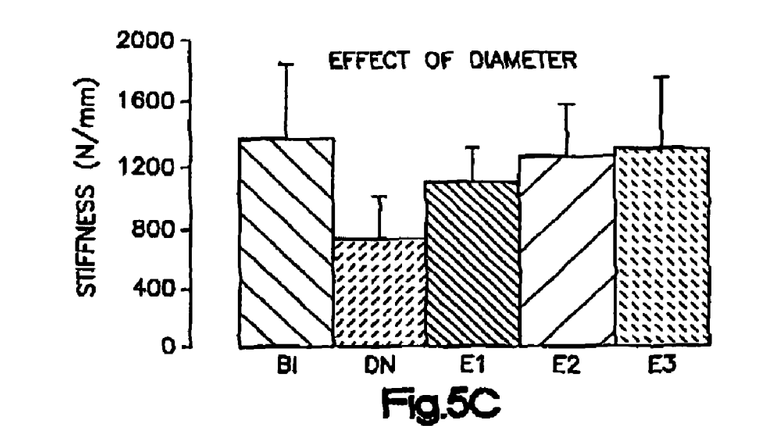

FIG. 5 shows that there was a statistical difference ($p<0.05$) between the compressive stiffness of $E_1$ and $E_2$, but not between $E_2$ and $E_3$. There is likely a threshold where the modulus will affect tensioning of the annulus fibers, after which, the lateral deformations associated with the higher modulus do nothing to further the stiffness of the system. The effect of height and diameter variation on the stiffness was significant. In the cases of both smaller height ($H_1$) and smaller diameter ($D_1$), lack of proper interaction between the hydrogel implant and intact annulus resulted in limited restoration of the denucleated ACU. In the cases of higher height ($H_3$) and larger diameter ($D_3$), almost complete restoration (99% of BI) of the stiffness was observed ($p>0.6$). The implant with higher geometric parameters ($H_3$ and/or $D_3$) may exert a pre-stress on the annulus fibers, pushing them radially outwards in the process of maintaining its constant volume. This probably mimics the natural load transfer phenomenon of the IVD, where intradiscal pressure creates tension in the annulus, even in a resting position.

The results of this example demonstrate that variations in geometric parameters (i.e., filling the implant to proper height and width) is more important for restoration of ACU compressive stiffness than variations in the moduli of the implant.

Example 9

Effect of Modulus of Elasticity

Figure 6:
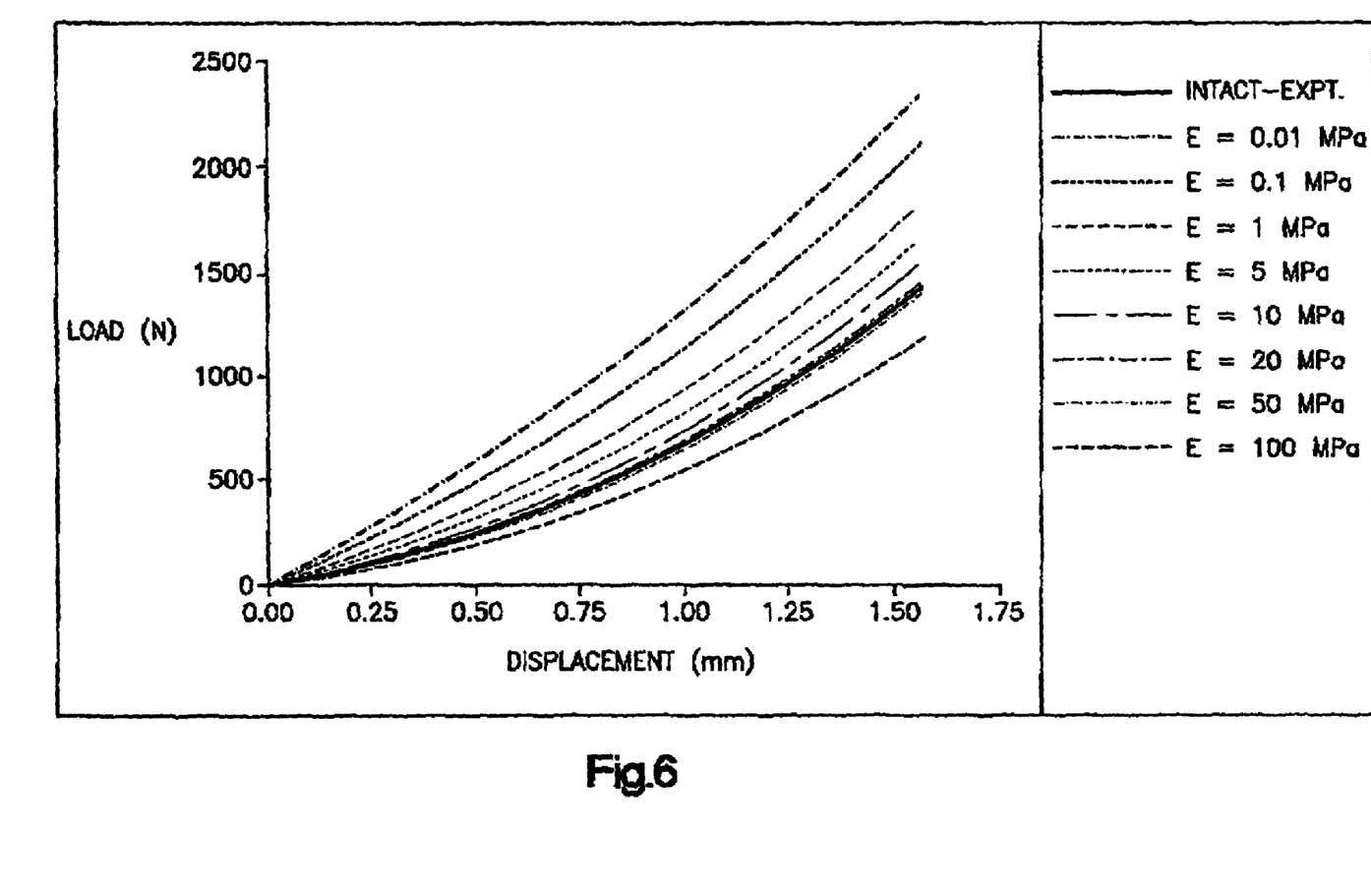
FIG. 6 illustrates the results of an implant modulus on the compressive stiffness of the intervertebral disc.

The effect of an implant modulus on the compressive stiffness of the intervertebral disc was also studied and the results of modulus ranging from 10 kPa to 100,000 kPa are described in FIG. 6 below. The wider range of 10 kPa to 10,000 kPa brings the compressive biomechanics within a close window to the normal range of a functional disc, while the normal mechanical behavior of the disc is restored in the range of 10-5,000 kPa. The modulus of elasticity requirements, therefore would be from 10 kPa to 10,000 kPa and more preferably from 10 kPa to 5000 kPa.

White the present invention has been described in the context of particular embodiments and examples, it will be readily apparent to those skilled in the art that other modifications and variations can be made without departing from the spirit or scope of the present invention. Accordingly, it is not intended that the present invention be limited to the specifics of the foregoing description of those embodiments and examples, but rather as being limited only by the scope of the invention as defined in the claims appended hereto.

What is claimed is:

1. A spinal disc augmentation implant for insertion into an intervertebral disc of a mammal comprising an injectable polymer solution comprising a poly(N-isopropyl acrylamide) chemically cross linked by a polyethylene glycol-based polymeric crosslinking agent so that the polymer solution solidifies from a liquid at room temperature to a solid or semi-solid hydrogel at physiological body temperature; wherein the ratio of poly(N-isopropyl acrylamide) to the polymeric crosslinking agent is from about 20 to 1 to about 500 to 1 and the implant has a modulus of elasticity between about 50 KPa and about 1,500 KPa.

2. The spinal disc augmentation implant according to claim 1, wherein the polymeric crosslinking agent is hydrophilic.

3. The spinal disc augmentation implant according to claim 1, wherein the polymer solution further comprises from about 25% to about 50% weight by volume of water.

4. The spinal disc augmentation implant according to claim 1 further comprising an imaging agent.

5. The spinal disc augmentation implant according to claim 4, wherein said imaging agent is selected from the group consisting of barium sulfate, iodine, and a heavy metal power.

6. A method of implanting a thermogelling hydrogel into an interior cavity of an intervertebral disc of a spinal column of a mammal, the method comprising injecting a hydrogel solution comprising poly(N-isopropyl acrylamide) chemically cross linked by a polyethylene glycol-based polymeric crosslinking agent into the interior cavity of the intervertebral disc of the spinal column; wherein the hydrogel solution is injected as a liquid at room temperature and solidifies to form a solid implant as the hydrogel solution warms to physiological body temperature; wherein the ratio of poly(N-isopropyl acrylamide) to the polymeric crosslinking agent is from about 20 to 1 to about 500 to 1 and the implant has a modulus of elasticity between about 50 KPa and about 1,500 KPa.

7. The method according to claim 6, wherein the polymeric crosslinking agent is hydrophilic.

8. The method according to claim 6, wherein the hydrogel solution further comprises from about 25% to about 50% weight by volume of water.

9. The method according to claim 6, wherein said hydrogel solution further comprises an imaging agent.

10. The method according to claim 6, wherein the thermogelling hydrogel is implanted for nucleus pulposus replacement.

11. The method according to claim 6, wherein the thermogelling hydrogel is implanted for nucleus pulposus augmentation.

12. A spinal disc augmentation implant for insertion into an intervertebral disc of a mammal comprising an injectable polymer solution comprising a poly(N-isopropyl acrylamide) chemically cross linked by a polyethylene glycol-based polymeric crosslinking agent so that the polymer solution solidifies from a liquid at room temperature to a solid or semi-solid hydrogel at physiological body temperature; wherein the ratio of poly(N-isopropyl acrylamide) to the polymeric crosslinking agent is from about 20 to 1 to about 500 to 1 and the implant has a modulus of elasticity between about 50 KPa and about 1,500 KPa; wherein the polymeric crosslinking agent comprises polyethylene glycol dimethylacrylate.

13. The method according to claim 6, wherein the polymeric crosslinking agent comprises polyethylene glycol dimethylacrylate.

14. A method of implanting a thermogelling hydrogel into an intervertebral disc space between adjacent vertebral bodies using a hydrogel solution comprising poly(N-isopropyl acrylamide) chemically cross linked by a polyethylene glycol-based polymeric crosslinking agent, wherein the ratio of poly(N-isopropyl acrylamide) to the polymeric crosslinking agent is from about 20 to 1 to about 500 to 1, the method comprising the steps of:
  a) forming an incision;
  b) inserting a cannula into communication with the intervertebral disc space to create a passageway to the disc space;
  c) inserting a needle into the intervertebral disc space via the cannula;
  d) injecting the hydrogel solution as a liquid at room temperature into the intervertebral disc space;
  e) permitting the hydrogel solution to solidify to form a solid implant as the hydrogel solution warms to physiological body temperature such that the solid implant has a modulus of elasticity between about 50 KPa and about 1,500 KPa;
  f) removing the needle and cannula; and
  g) closing the incision.

15. The spinal disc augmentation implant according to claim 1, wherein room temperature is between 22° C. and 27° C. and body temperature is between 29° C. and 37° C.

16. The method of claim 6, wherein room temperature is between 22° C. and 27° C. and body temperature is between 29° C. and 37° C.

17. The method of claim 14, wherein room temperature is between 22° C. and 27° C. and body temperature is between 29° C. and 37° C.

* * * * *